US00PP09242P

United States Patent [19]

Cowles et al.

[11] Patent Number: Plant 9,242

[45] Date of Patent: Aug. 15, 1995

[54] 'PEARL STREET' PISTACHE

[75] Inventors: Peter Cowles; Allen Lagarbo, both of Modesto, Calif.

[73] Assignee: City of Modesto, Modesto, Calif.

[21] Appl. No.: 320,132

[22] Filed: Nov. 28, 1994

[51] Int. Cl.[6] ..... A01H 5/00

[52] U.S. Cl. ..... Plt./51.1

[58] Field of Search ..... Plt. 51.1

*Primary Examiner*—James R. Feyrer

[57] ABSTRACT

A novel male Chinese pistache tree is described, characterized by rapid growth and large trunk caliper in budded nursery stock, upright growing branches that average 52 degree branch attachments, trunk and scaffold branches with strong apical dominance, and a tall, dense, globe-shaped crown.

3 Drawing Sheets

The present invention relates to a new and distinct male variety of Chinese Pistache tree of the species botanically known as *Pistacia chinensis.* We have named our new variety 'Pearl Street'. We discovered this new variety as a chance seedling of unknown parentage growing as a planted street tree near Pearl Avenue in Modesto, Calif.

This individual tree had been noticed for nearly ten years for having grown tall and rigidly upright. The other 6,000 plus Pistache trees within the City are more open and spreading with a lower scaffold pattern and shorter overall height. The 'Pearl Street' is unique in its upright growing habit.

Close observations of this seedling and continued observations of progeny thereof subsequently asexually propagated under the Arborist direction by budding on seedling *Pistacia chinensis* under stock, has confirmed that the unique characteristics of this new variety are a result of a seedling variation. We are therefore convinced that our new tree represents a new and improved variety of *Pistacia chinensis,* as particularly evidenced by the following unique combination therein, and which distinguish this new variety from other varieties of this species:

1. A unique habit of growth resulting in a denser, upright branched crown that is broadly globe-shaped and taller than the species or the 'Keith Davey' variety;

2. Scaffold branches upright and forming higher on the trunk. Primary scaffolds showing stronger apical dominance than the species or the 'Keith Davey' variety;

3. A growth rate which is much faster than the species or 'Keith Davey' from budded starts (bud shoots pushing 18–24 inches the first season; second season shoots reaching 5–7 feet in height);

4. Trunks are vertical and well-tapered showing strong apical dominance with little or no side shoots until the primary scaffolds appear; and;

5. Secondary and tertiary scaffolds continue to be angled upward as they grow with few, if any, horizontal or down turned branches. Branch attachments are strong.

The accompanying photographs depict the color of the invention which is similar to the species, yellow-orange to orange-red.

Figure 2:
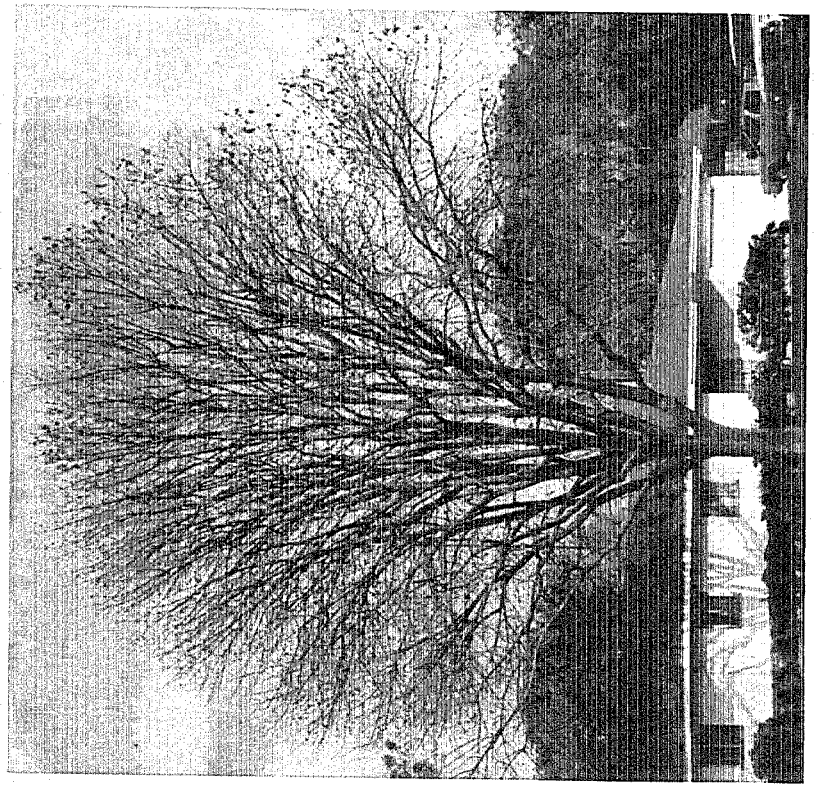
FIG. 2 is a color photograph of the crown in winter dormancy showing the form and branching structure of the present invention.
Figure 1:
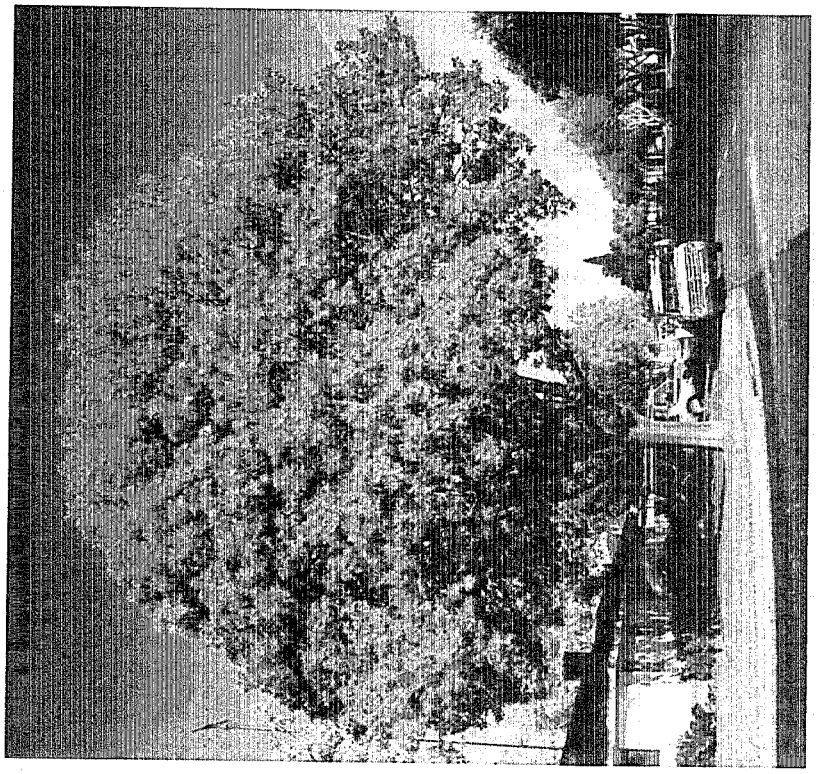
FIG. 1 is a color photograph of the present invention in fall color.
Figure 4:
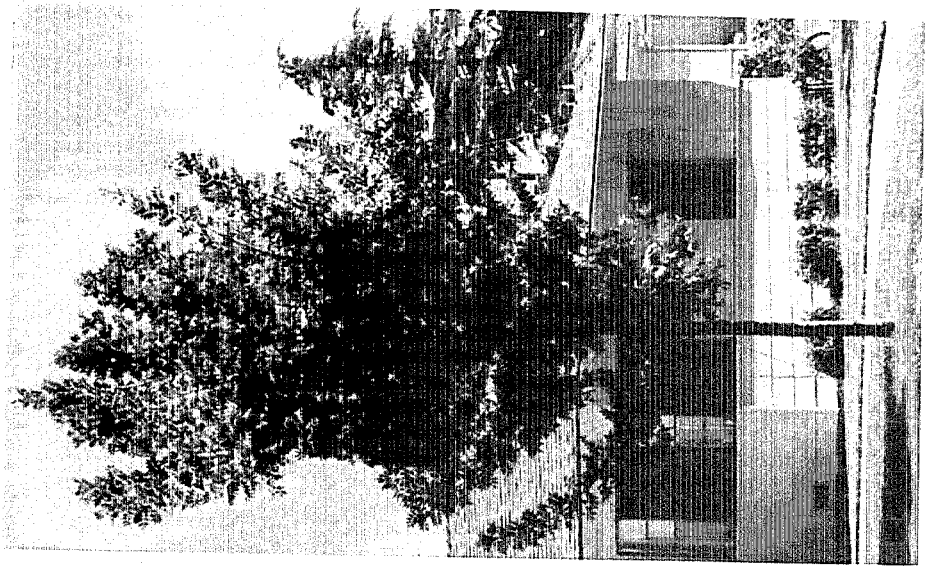
FIG. 4 is a color photograph of a 4-year-old tree of the present invention showing the upright growth.
Figure 3:
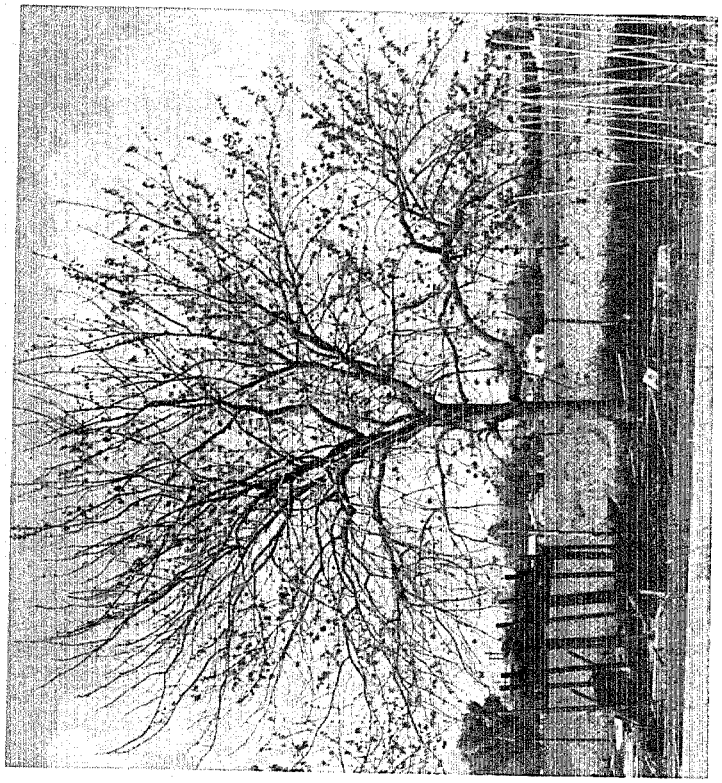
FIG. 3 is a color photograph of the crown in winter dormancy showing the typical form and branching structure of the species *Pistacia chinensis;*
Figure 5:
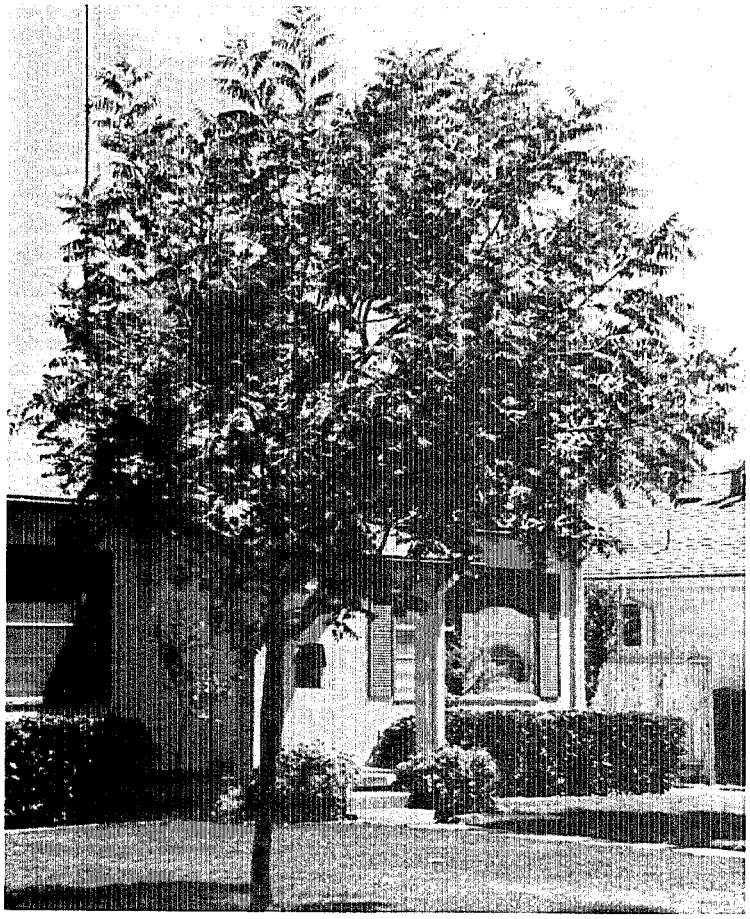
FIG. 5 is a color photograph of a typical 5-year-old tree of the species *Pistacia chinensis.
Figure 6:
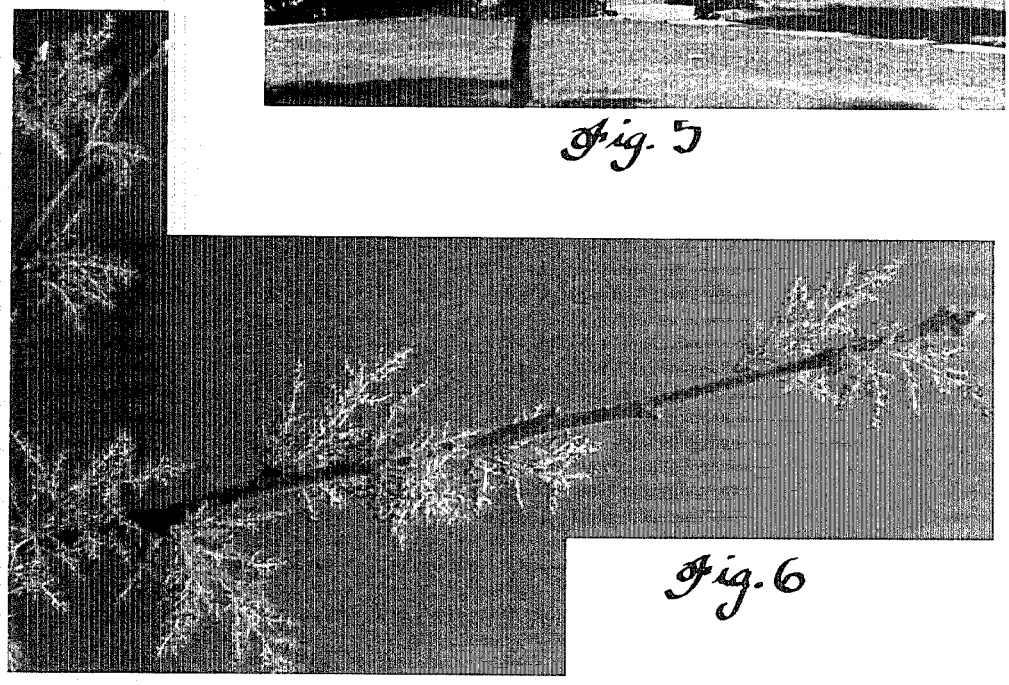
* and FIG. 6 is a color photograph of the male inflorescence of the present invention.

One of the primary distinguishing features of our new tree is the rapid and vigorous growth observed in young nursery stock. The average caliper of 2-year-old budded 'Pearl Street' trees has proven to be greater than the caliper of seedling Pistache grown in similar environments. The larger caliper and vigorous vertical growth requires less nursery staking and training and produces a tree less dependant on staking as a permanent planting.

Table I sets forth a comparison of the caliper size of seedling Pistache and the 'Pearl Street' variety Pistache, 2-year-old nursery stock. The caliper of 100 trees of each type were compared to determine this distribution. Measurements were made 2 inches above the soil level on the seedling Pistache and 2 inches above the bud union on the 'Pearl Street'.

TABLE I

CALIPER SIZE DISTRIBUTION OF 2-YEAR-OLD NURSERY TREES

| Caliper | Seedling | 'Pearl' |
|---|---|---|
| 0–½" | 18% | 1% |
| ⅝% | 38% | 9% |
| ¾% | 31% | 33% |
| ⅞% | 10% | 35% |
| 1"–> | 3% | 22% |

The second season after budding primary scaffold branches can be identified. During the third season after budding, the new variety exhibits increased dominance of two to four primary scaffold branches. The scaffolds grow nearly vertical, developing from branch attachments that have been observed at angles of 35 degrees to 85 degrees, averaging 52 degrees. Branch angles and observed apical dominance is distinct from seedling Pistache and the 'Keith Davey' variety. These important elements of branch angle and crown development predominate as a permanent growth pattern of this new variety.

Table II compares the distribution of branch angles of primary and secondary scaffold branches on 4-year-old trees of our new variety of Pistache, seedling Pistache, and the 'Keith Davey' variety of Pistache. The branch angles of ten trees of each variety were compared to determine this distribution.

TABLE II

| Branch Angle | BRANCH ANGLE DISTRIBUTION ON FOUR YEAR OLD TREES | | |
|---|---|---|---|
| | 'Pearl Street' | Seedling | 'Keith Davey' |
| 0–35 | 4% | 0% | 0% |
| 40 | 14% | 8% | 8% |
| 45 | 32% | 26% | 12% |
| 50 | 10% | 6% | 0% |
| 55 | 6% | 12% | 10% |
| 60 | 12% | 2% | 20% |
| 65 | 14% | 0% | 8% |
| 70 | 2% | 4% | 0% |
| 75 | 4% | 8% | 10% |
| 80 | 0% | 16% | 14% |
| 85 | 2% | 12% | 8% |
| 90 | 0% | 6% | 12% |
| (Average) | (52 degrees) | (62 degrees) | (68 degrees) |

In generating Tables I and II, comparisons were made of the specified varieties growing in the City of Modesto tree nursery and trees permanently planted as City of Modesto street trees.

Branch attachments are strong for the new variety with no limb breakage observed. The seedling Pistache tree and the 'Keith Davey' have been observed to have limb breakage because of horizontal growing branches becoming heavy and failing.

The upright branches of the new variety require less pruning within the drip line of the crown for building and roadway clearance allowing this variety to have a wider range of uses in an urban environment.

The following is a detailed description of our new variety of *Pistacia chinensis* tree:

Parentage: A chance seedling of unknown parentage.

Propagation: Holds to distinguishing characteristics through a succeeding propagation by budding.

Localities where grown and observed: Modesto, Calif.

Tree: Dense, globe-shaped crown with upright branches.

Growth rate: Relatively fast growth rate than that of the seedling pistache or the 'Keith Davey' variety grown under comparable conditions in a nursery.

Height: 40–45 feet.

Leaf color: Leaf summer color is a green color (similar to RHS 136a or 135a). In the Fall, leaves turn to a yellow-orange through an orange-red color (similar to RHS 17c and RHS 44b). Colors are similar to the species.

Branch angle: Four-year-old trees have primary and secondary scaffold branch angles that average 52 degrees, with an observed range of 35 to 85 degrees.

Foliage: Deciduous.

*Leaves.*—Alternate, odd- or even- pinnately compound

*Leaf size.*—Length—6 to 10 inches

*Leaflet size.*—Length—typically $1\frac{7}{8}$ to 3 5/16 inches; breadth typically 7/16 to 1 5/16 inches.

*Leaflet shape.*—Lanceolate.

*Leaflet margin.*—Entire.

*Leaflet tip.*—Acuminate.

*Leaflet base.*—Oblique.

*Number of leaflets.*—8 to 15.

*Flower.*—Staminate only, small in dense panicles, 2 to 3 inches in length.

We claim:

1. A new and distinct variety of Chinese Pistache tree, substantially as herein shown and described, characterized particularly as to novelty by a high percentage of upright scaffold branches growing nearly vertical on 4-year-old trees, with solid attachments and a narrower branch angle than that of the Seedling Pistache and the 'Keith Davey' variety; superior apical dominance resulting in heavy caliper of trunk and rapid growth of young budded nursery stock 2 years old.

* * * * *